United States Patent [19]
Pechter

[11] Patent Number: 5,965,809
[45] Date of Patent: Oct. 12, 1999

[54] METHOD OF BRA SIZE DETERMINATION BY DIRECT MEASUREMENT OF THE BREAST

[76] Inventor: Edward Pechter, 25880 Tournament Rd, #217, Valencia, Calif. 91355

[21] Appl. No.: 09/149,186

[22] Filed: Sep. 8, 1998

Related U.S. Application Data

[60] Provisional application No. 60/057,838, Sep. 8, 1997.

[51] Int. Cl.[6] ................................................. G01F 17/00
[52] U.S. Cl. ................................................................ 73/149
[58] Field of Search .................... 73/149, 429; 128/774, 128/778; 33/2 R, 262, 511, 512, 759

[56] References Cited

U.S. PATENT DOCUMENTS

| | | | |
|---|---|---|---|
| 2,524,028 | 10/1950 | Bordner | 33/512 X |
| 2,527,206 | 10/1950 | Amyot | 33/512 X |
| 2,559,501 | 7/1951 | Graf | 33/512 X |
| 2,575,343 | 11/1951 | Heiman | 33/512 X |
| 2,946,125 | 7/1960 | Gittelson . | |
| 4,219,029 | 8/1980 | Grossman et al. | 73/149 X |
| 4,279,259 | 7/1981 | Lee et al. | 128/774 |
| 4,624,671 | 11/1986 | Kress | 73/149 X |
| 5,414,943 | 5/1995 | Vogt | 33/512 X |
| 5,485,855 | 1/1996 | Shiraiwa et al. | 128/774 |
| 5,619,804 | 4/1997 | Vogt et al. | 33/763 |

*Primary Examiner*—Benjamin R. Fuller
*Assistant Examiner*—Jewel V. Thompson
*Attorney, Agent, or Firm*—Roger A. Marrs

[57] ABSTRACT

This relates to a method of direct measurement to determine cup size of the breast which includes band size measurement by initially measuring the user's chest or torso circumference with a flexible tape measure immediately below the breasts followed by the step of adding five inches to the measured number and incorporating conventional rounding-off procedures. Next, cup size is determined by directly measuring with the tape the circumference of each unclothed breast from the beginning of the breast mound at one side laterally to the parasternal area medially. Next, a measurement conversion is made wherein a measurement of seven inches corresponds to an "A" size cup, eight inches a "B" size cup, nine inches a "C" cup, etc. Each one inch increment determines a cup size.

8 Claims, 1 Drawing Sheet

METHOD OF BRA SIZE DETERMINATION BY DIRECT MEASUREMENT OF THE BREAST

Priority claimed based on Ser. No. 60/057,838 filed Sep. 8, 1997.

BACKGROUND OF THE INVENTION

1. Field of the Invention

The present invention relates to the field of medical procedures, and more particularly to a novel method for determining the bra size of a woman's breast by direct measurement of the breast.

2. Brief Description of the Prior Art

It is often reported that 70% or more of women wear the wrong size bra. It appears that the current method or procedure of determining women's bra size is unreliable a majority of the time. The traditional method of bra measurement is complicated and often yields an improper size which does not correlate to a woman's correct and proper cup size. Improper size renders the wearing of such a bra uncomfortable and may cause other medical problems. Specifically, conventional bra size is determined by two measurement factors such as the "band size" and "cup size".

The band size is expressed in inches while the cup size is represented by a letter such as A, B, C, etc. Band size is determined by measuring the wearer's chest circumference snugly with an incremented tape immediately below the breasts and around the torso. Then five inches is added to the chest circumference measurement. If the sum is an odd number, the sum is rounded to the next highest even number since bras are offered in "even" numbered sizes. Although band size relates to cup size and may continue to be included in a measurement procedure, only the cup size measurement is considered obsolete. The determination of band size is relatively objective compared to the usual subjective method of determining cup size.

The traditional method of determining cup size does not rely on direct measurement of the breast but instead relates to measurement of the circumference of the chest or torso immediately below the breast, sometimes referred to as chest circumference, diaphragm size or body size, etc., to the circumference of chest around the fullest part of the breasts sometimes referred to as bust measurement, cup size, bust size, breast size or bosom. Cup size is determined by comparing band size with bust measurement, the latter being determined by measuring the circumference of the chest loosely with a measuring tape around the fullest part of the breasts, usually at the level of the nipples, with the woman wearing a bra. A difference of one inch equals an A cup, two inches a B cup, three inches a C cup, and so on.

It appears that the goal of the conventional method of determining bra measurement seems to be to determine cup size by comparing the circumference of the chest at the level of the breasts to the same measurement excluding the breasts. Since the latter measurement cannot be made directly, the addition of five inches to the underbust measurement represents an extrapolation or "fudge factor" to approximate that goal.

To compensate for measurement or extrapolation error, elastic is placed in the band of the bra as well as adjustable attachment means which are used to connect the opposite ends of the bra band together. Separate elastic compensating tabs or extensions are used to extend the length of the bra and in some instances multiple rows of attachment loop and hooks are employed to achieve compensation.

Therefore, a long-standing need has existed to provide a new method or procedure for determining proper bra size by utilizing direct breast measurement techniques, especially the technique of determining cup size by measuring the circumference of an unclothed breast.

One attempt to provide a bust measurement device is disclosed in U.S. Pat. No. 2,946,125 which pertains to a harness-type apparatus having an adjustable horizontal measuring tape or strip and at least a pair of vertically disposed measuring tapes or strips that are trained through spaced-apart slots in the horizontal tape. The device is not believed to be pertinent since no attempt is made to measure band, chest or torso size or girth as a necessary measurement to be used with breast measurement in order to determine cup size. Also, the device requires that the user wear the device while measurement is being taken.

SUMMARY OF THE INVENTION

The above problems and difficulties are avoided by the novel method of direct measurement to determine cup size of the breast. The method includes band size measurement by initially measuring the user's chest or torso circumference with a tape measure immediately below the breasts followed by the step of adding five inches to the measured number and incorporating conventional rounding off procedures. Next, cup size is determined by directly measuring with a flexible tape measure the circumference of each unclothed (bare) breast from the beginning of the breast mound at one side laterally to the parasternal area medially. In some instances, measurements are taken while the woman is standing and in other instances, the woman is in a supine position. Next, a measurement conversion is made wherein a measurement of seven inches corresponds to an "A" size cup, eight inches a "B" size cup, nine inches a "C" cup, etc. Each one inch increment determines a cup size.

Therefore, it is among the primary objects of the present invention to provide a novel method for bra size determination which employs direct measurement of the breast while the breast is in an unclothed condition.

Another object of the present invention is to provide a novel method for determining bra size wherein the measuring of the breast is done with an incremented tape for determining the circumference of an unclothed breast from the beginning of the breast mound laterally to the parasternal area medially.

Another object of the present invention is to provide a novel method of determining cup size by comparing the measurement of an unclothed breast to bust measurement.

Still a further object of the present invention is to provide a novel method of determining cup size by directly measuring breast circumference in inches and converting the measurement to an alphabetic indication wherein each one inch of measurement increment determines a cup size up or down.

Another object resides in providing a bra size determination which corresponds to a woman's own estimation of cup size and which makes the purchase of a brassiere simpler and more accurate as well as providing plastic surgeons a means to communicate more effectively with patients undergoing breast augmentation and reduction surgery.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

DESCRIPTION OF THE PREFERRED EMBODIMENT

Figure 1:
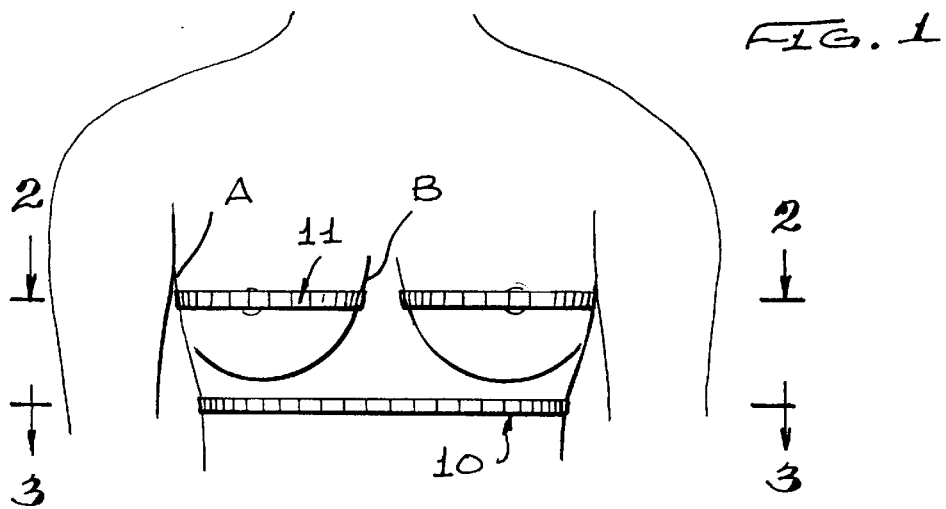
FIG. 1 is a front elevational view illustrating the direct measurement of breasts in accordance with the method of the present invention.

Referring to FIG. 1, a woman's torso is illustrated and it is to be particularly noted that the measurements to be taken by the inventive method are performed about unclothed breasts. The first step in performing the method is to determine proper band size which is determined by measuring the chest or torso circumference employing a tape measure 10 which is preferably in increments of inches. The tape is placed about the chest in a snug fashion immediately below the breasts. After the measure of increment has been noted, a resultant figure is then tabulated and may be used to determine the length of the bra band. However, in employing the inventive method, the resultant measurement need not be used to determine cup size.

In determining cup size, the woman's breast intended to be measured is unclothed and cup size is determined by direct measurement of the bare breast. Each breast is measured separately so that separate tabulation for a cup relating to each breast may be noted. Direct measurement is achieved by measuring with a flexible tape measure, the circumference of the unclothed breast from the beginning of the breast mound as at point A laterally across the breast mound at the nipple into the parasternal area medially as represented by B. In small or firm breasts, this measurement can readily be achieved while the woman is standing. Whereas with woman with large or ptotic breasts, a more accurate measurement can be achieved with the woman in a supine position. The point where the breast mound begins, A, laterally can sometimes be more easily discerned in a heavy woman with her arms elevated. A measurement of seven inches corresponding to an "A" cup is a conversion factor. Likewise, a measurement of eight inches would represent a "B" cup while nine inches represents a "C" cup and so on up and down the measurement line with each one inch increment determining a cup size up or down. The flexible tape measure for measuring directly over the unclothed breast is indicated by numeral 11.

Figure 2:
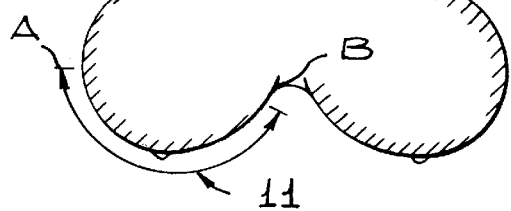
FIG. 2 is a transverse cross-sectional view of the torso as taken in the direction of arrows 2—2 of FIG. 1.

Referring now in detail to FIG. 2, the breast mound is shown to start at points A and B with the measurement taken between A and B so as to directly establish cup size when the measurement is converted.

Figure 3:
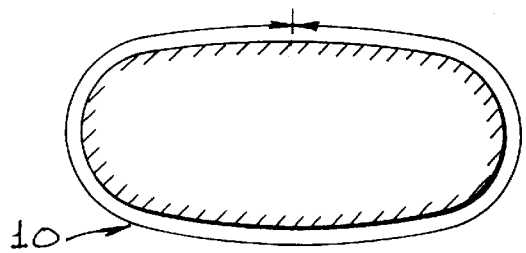
FIG. 3 is a transverse cross-sectional view of the torso as taken in the direction of arrows 3—3 of FIG. 1.

FIG. 3 illustrates the use of an incremented tape 10 for determining band size should this be useful in determining the length of bra band. However, it is again noted that band size is not necessary for determining cup size when practicing the inventive method.

Figure 4:
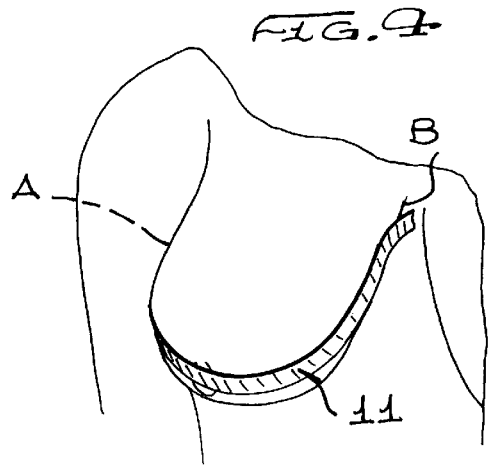
FIG. 4 is a perspective view showing the method of measuring a breast in accordance with the method of the present invention.

Referring to FIG. 4, it can be seen that the inventive method can also be used successfully for measuring a breast which is large or ptotic by employing the tape 11 in the same manner as previously described. The measurement occurs across the fullness of the breasts past the nipple and terminates at positions A and B.

Figure 5:
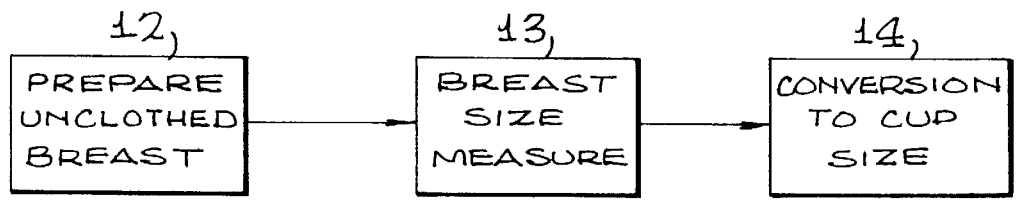
FIG. 5 is a block diagram illustrating the basic procedure for direct breast measurement.

Referring now in detail to FIG. 5, the method is illustrated in block diagram form wherein block 12 represents the preparatory step of unclothing the breasts so that they are bare and exposed. The next step in the method if to measure the distance from point A to point B by means of tape 11 and to extract the increment, such as in inches, and this step is represented by block 13. Next, a conversion is performed, as indicated by block 14, whereby the measured increment from step 13 is converted to a cup size represented by an alphabetic letter. As previously noted, a measurement of seven inches corresponds with an "A" cup, eight inches a "B" cup, nine inches a "C" cup, and so on. It is to be particularly noted that each one inch increment determines a cup size either up or down.

Therefore, it can be seen that the inventive method provides a single measurement for determining cup size and that the measurement is direct for each breast and that measurement is extremely convenient, accurate and would be of great help to plastic surgeons by affording them the opportunity of better meeting the expectations of women undergoing breast augmentation or reduction surgery. The current popular and traditional system of determining bra size is so often inaccurate as to be practically useless. The improved method of determining cup size by directly measuring the circumference of the breast itself is accurate and provides a cup size which will insure comfort and convenience to the user. If combined with determination of band size by direct correlation with underbust circumference, it is possible to dramatically reduce the number of women wearing the "wrong size bra".

It is to be further noted that a single length of measuring tape is employed for taking all measurements and that the need for the user to wear a harness-like apparatus with shoulder and torso bands or straps is totally unnecessary and undesirable. The tape measure may be stored on a resilient spool in a case or housing and may be drawn from the case or housing to a desired length. Numerical increments in inches or, if desired, millimeters are imprinted along either one or both edges of the tape. The woman may take measurements by herself using a mirror or by visual observation. However, it is recommended that an experienced or trained person assist in measurement.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A method of obtaining chest measurement for determining bra size by combining direct measurement and additive numerical data comprising the steps of: partially determining band size measurement by directly measuring the torso immediately below the breasts using a measurement tape to obtain a torso circumference number; completing the determination of band size by adding five inches to said measured torso circumference number; determining band size and cup size includes solely using a single length of flexible measuring tape having numerical indicia in terms of inches along the length of the tape; and partially determining breast cup size by directly measuring the circumference of each unclothed breast from the beginning of the breast mound at one side thereof laterally across the breast to terminate at the parasternal area medially; completing the determination of breast cup size by converting said direct breast measurement of each breast to a cup size corresponding to each one inch of measurement increment to an "A" size cup, a "B" size cup, a "C" size cup and so on in a predetermined sequence.

2. The method defined in claim 1 wherein the determining steps of measuring for band size and cup size are taken with a woman in standing position.

3. The method defined in claim 1 wherein the determining steps of measuring for band size and cup size are taken with a woman in a supine position.

4. The method defined in claim 1 wherein the step of determining breast cup size includes separate measurement of each breast in a bare state across the breast nipple from one side to the other side of each breast.

5. The method defined in claim 4 wherein the steps of determining band size and cup size include solely using a single length of flexible measuring tape having numerical indicia in terms of inches along the length of the tape.

6. The method defined in claim 1 wherein the step of completing the determination of breast cup size further includes a measurement conversion wherein a measurement of seven inches corresponds to the "A" cup eight inches corresponds to the "B" cup, nine inches corresponds to the "C" cup and continues for each one inch increment.

7. A method of direct measurement of breasts to determine bra size for the breast of a woman comprising the steps of:

determining band size measurement by employing a two step procedure consisting of an initial measuring procedure and a calculation procedure; said initial measuring procedure includes measuring the woman's torso circumference with a flexible tape measure by encircling the torso immediately below the breasts and noting the measurement in increments of inches to obtain a measured number; said calculation procedure includes calculating the band size by adding five inches to the measured number employing rounding-off to the next higher even number;

determining cup size for each breast separately by directly measuring each breast includes solely using a single length of flexible measuring tape having numerical indicia in terms of inches along the length of the tape measure by employing a two step procedure consisting of a breast measuring procedure and a measurement conversion procedure;

said breast measuring procedure includes measuring the circumference of each unclothed breast from the beginning of the breast mound at one side laterally across the nipple to the parasternal area medially while the woman is either in a preselected standing or a supine position depending upon the woman's overall size, shape and weight; and said measurement conversion procedure includes performing a measurement conversion using the breast circumference measurement as a base wherein a measurement of seven inches corresponds to an "A" size cup, eight inches corresponds to a "B" size cup, nine inches corresponds to a "C" size cup and so forth whereby each one inch increment determines a cup size.

8. A method for direct and exact measurement of breasts to determine bra cup size for each breast of a woman comprising the steps of:

using solely a single elongated flexible tape;

placing the flexible tape across the circumference of each unclothed breast with one end of the tape at the beginning of the breast mound at one side thereof and extending the flexible tape laterally across the nipple to the parasternal area medially while the woman is either in a preselected standing or supine position depending upon the woman's physical condition and breast shape so as to result in a breast circumference for each breast respectively; and establishing a measurement conversion by utilizing the breast circumference measurement for each breast as a base wherein a measurement of seven inches corresponds to an "A" size cup, eight inches corresponds to a "B" size cup, nine inches corresponds to a "C" size cup and so forth whereby each one inch increment determines a cup size.

* * * * *